(12) United States Patent
Clark et al.

(10) Patent No.: US 9,594,077 B2
(45) Date of Patent: Mar. 14, 2017

(54) METHODS AND REAGENTS FOR EVALUATING THE BINDING OF MAMMALIAN SPERM

(71) Applicant: The Curators of the University of Missouri, Columbia, MO (US)

(72) Inventors: Gary Francis Clark, Columbia, MO (US); Peter Sutovsky, Columbia, MO (US)

(73) Assignee: The Curators of the University of Missouri, Columbia, MO (US)

(*) Notice: Subject to any disclaimer, the term of this patent is extended or adjusted under 35 U.S.C. 154(b) by 0 days.

(21) Appl. No.: 14/412,318

(22) PCT Filed: Jul. 3, 2013

(86) PCT No.: PCT/US2013/049349
§ 371 (c)(1),
(2) Date: Dec. 31, 2014

(87) PCT Pub. No.: WO2014/008413
PCT Pub. Date: Jan. 9, 2014

(65) Prior Publication Data
US 2015/0168382 A1 Jun. 18, 2015

Related U.S. Application Data

(60) Provisional application No. 61/690,729, filed on Jul. 3, 2012.

(51) Int. Cl.
*G01N 33/50* (2006.01)
*G01N 33/569* (2006.01)

(52) U.S. Cl.
CPC ......... *G01N 33/5091* (2013.01); *G01N 33/50* (2013.01); *G01N 33/56966* (2013.01); *G01N 2400/38* (2013.01); *G01N 2800/367* (2013.01)

(58) Field of Classification Search
CPC .................................................... G01N 33/50
See application file for complete search history.

(56) References Cited

U.S. PATENT DOCUMENTS

| 5,897,988 A | 4/1999 | Huszar |
| 7,148,021 B2 | 12/2006 | Chi et al. |

OTHER PUBLICATIONS

Yonezawa et al. Molecular Reproduction and Development, 2005, 70:222-227.*
Oda et al. JBC, 2003, 278(34):32439-32447.*
Bleil et al., "Identifaction and Characterization of Proteins of Zona Pellucida", The Journal of Cell Biology, 1978, p. A173, vol. 79.
Clark et al., "The Mammalian Zona Pellucida: A Matrix that Mediates Both Gamete Binding and Immune Recognition?", Systems Biology in Reproductive Medicine, 2010, pp. 349-364, vol. 56.

Dam et al., "Thermodynamics of Multivalent Carbohydrate-Lectin Cross-Linking Interactions: Importance of Entropy in the Bind and Jump Mechanism", Biochemistry, 2009, pp. 3822-3827, vol. 48.
Dunbar et al., "Isolation and Physicochemical Properties of Porcine Zona Pellucida", The Journal of Cell Biology, 1978, p. A163, vol. 79.
Hedrick et al., "Anuran and Pig Egg Zona Pellucida Glycoproteins in Fertilization and Early Development", The International Journal of Developmental Biology, 2008, pp. 583-701, vol. 52.
Lopo et al., "Sperm-Egg Binding Events During Sea Urchin Fertilization", Annals of the New York Academy of Sciences, 1982, pp. 405-425, vol. 383.
Mengerink et al., "Glycobiology of Sperm-Egg Interactions in Deuterostomes", Glycobiology, 2001, pp. 37R-43R, vol. 11.
Nakano et al., "Structure and Function of the N-Linked Carbohydrate Chains of Pig Zona Pellucida Glycoproteins", Journal of Reproduction and Fertility Supplement, 1996, pp. 25-34, vol. 50.
Noguchi et al., "Structural Characterization of the N-Linked Carbohydrate Chains from Mouse Zona Pellucida Glycoproteins ZP2 and ZP3", Biochimica et Biophysica Acta, 1993, pp. 217-226, vol. 1158.
North et al., "Mass Spectrometry in the Analysis of N-Linked and O-Linked Glycans", Current Opinion in Structural Biology, 2009, pp. 498-506, vol. 19.
Pang et al., "Human Sperm Binding is Mediated by the Sialyl-Lewis(x) Oligosaccharide on the Zona Pellucida", Science, 2011, pp. 1761-1764, vol. 333.
Sutton-Smith et al., "Analysis of Protein-Linked Glycosylation in a Sperm-Somatic Cell Adhesion System", Glycobiology, 2007, pp. 553-567, vol. 17.
Tulsiani et al., "Mammalian Fertilization: A Carbohydrate Mediated Event", Biology of Reproduction, 1997, pp. 487-494, vol. 57.
Vacquier et al., "Isolation of Bindin: The Protein Responsible for Adhesion of Sperm to Sea Urchin Eggs", Proceedings of the National Academy of Science, 1977, pp. 2456-2460, vol. 74.
Yanagimachi et al., "Mammalian Ferilitzation", Physiology of Reproduction, 1994, pp. 169-317, Raven Press, New York.
Hirano et al., "O-Linked Neutral Sugar Chains of Porcine Zona Pellucida Glycoproteins", European Journal of Biochemistry. Jun. 1993, pp. 763-769, vol. 214.
Marti et al., "The N-and O-Linked Carbohydrate Chains of Human, Bovine and Porcine Plasminogen", European Journal of Biochemistry, Apr. 1998, pp. 57-63, vol. 173.
Xu et al., "In Vitro Reconstitution of the Modulation of *Drosophila* Notch-Ligand Binding by Fringe", Journal of Biological Chemistry, Oct. 8, 2007, pp. 35153-35162, vol. 282.
Barbato et al., "A Practical in Vitro Sperm-Egg Binding Assay that Detects Subfertile Males", Biology of Reproduction, Mar. 1, 1998, pp. 686-699, vol. 58, No. 3, Academic Press, New York, New York.

(Continued)

*Primary Examiner* — Bin Shen
(74) *Attorney, Agent, or Firm* — Thompson Coburn LLP

(57) ABSTRACT

The present invention provides a new apparatus/system for determining fertility of mammalian sperm based on a specific sperm-binding test that mimics sperm binding to an egg. The inventive apparatus/system comprises surface-modified beads with a compound or conjugates containing a carbohydrate sequence associated with the mammalian zona-pellucida (ZP) glycoproteins.

7 Claims, 1 Drawing Sheet

(56) References Cited

OTHER PUBLICATIONS

Kudo et al., "Localization of Carbohydrate Chains of Pig Sperm Ligand in the Glycoprotein ZPB of Egg Zona Pellucida" European Journal of Biochemistry, Mar. 15, 1998, 492-499, vol. 252, No. 3.
Noguchi et al., "Structural Analysis of the N-Linked Carbohydrates Chains of the 55-KDA Glycoprotein Family (PZP3) from Porcine Zona Pellucida", European Journal of Biochemistry, Mar. 15, 1992, pp. 1089-1100, vol. 204, No. 3.
Whitmarsh et al., "Biological Activity 1-15 of Recombinant Human ZP3 Produced in Vitro: Potential for a Sperm Function Test", Molecular Human Reproduction, Jan. 1, 1996, pp. 911-919, vol. 2, No. 12, Oxford University Press.
Yonezawa et al., "Molecular Cloning of Bovine Zona Pellucida Glycoproteins ZPA and ZPB and Analysis for Sperm-Binding Component of the Zona", European Journal of Biochemistry, Jun. 1, 2001, pp. 3587-3594, vol. 268, No. 12.
Yonezawa et al., "Recombinant Porcine Zona Pellucida Glycoproteins Expressed in Sf9 Cells Bind to Bovine Sperm but not to Porcine Sperm", Journal of Biological Chemistry, May 27, 2005, pp. 20189-20196, vol. 280, No. 21.
Yonezawa et al., "Identification of an N-Glycosylated Region of Pig Zona Pellucida Glycoprotein ZPB that is Involved in Sperm Binding", European Journal of Biochemistry, Aug. 15, 1997, pp. 86-92, vol. 248, No. 1.
Yurewicz et al., "Hetero-Oligomerization-Dependent Binding of Pig Oocyte Zona Pellucida Glycoproteins ZPB and ZPC to Boar Sperm Membrane Vesicles", Journal of Biological Chemistry, Mar. 27, 1998, pp. 7488-7494, vol. 273, No. 13.
Yurewicz et al., "Porcine Zona Pellucida ZP3-Alpha Glycoprotein Mediates Binding of the Biotin-Labeled M-r 55,000 Family (ZP3) to Boar Sperm Membrane Vesicles", Molecular Reproduction and Development, 1993, pp. 382-389, vol. 36, No. 3.
Extended European Search Report for EP Application 13813119.8 dated Feb. 3, 2016.

* cited by examiner

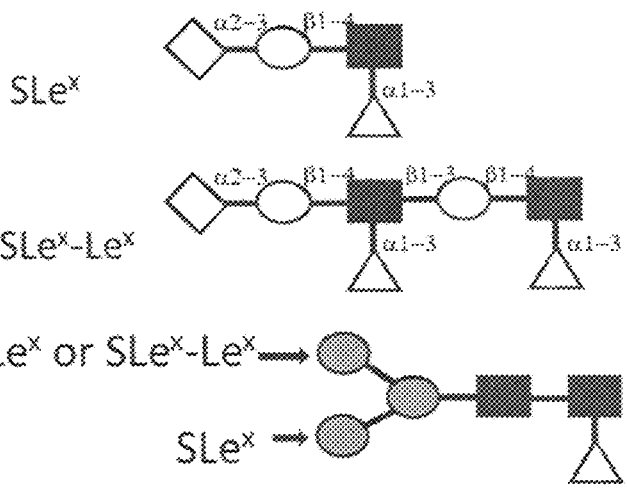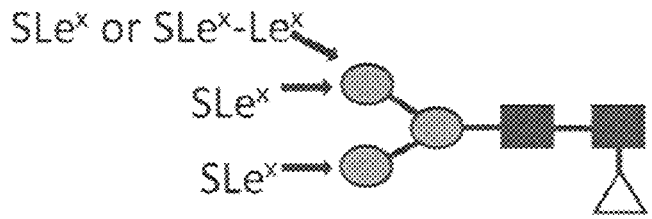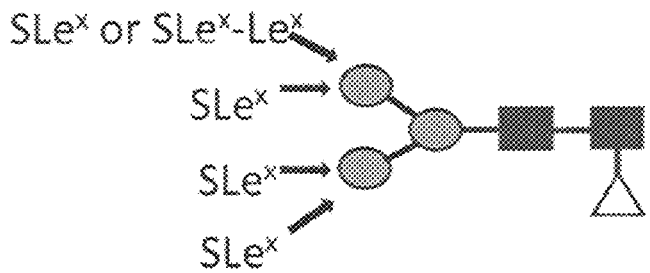
Prior Art

METHODS AND REAGENTS FOR EVALUATING THE BINDING OF MAMMALIAN SPERM

CROSS-REFERENCE TO RELATED APPLICATIONS

This patent application is a 35 U.S.C. §371 National Phase of International Patent Application No. PCT/US2013/049349, filed Jul. 3, 2013 and incorporated herein by reference in its entirety, which claims priority to provisional U.S. patent application Ser. No. 61/690,729, filed Jul. 3, 2012, the entire disclosure of which is incorporated herein by reference.

STATEMENT REGARDING FEDERALLY SPONSORED RESEARCH

This invention was made with Government support under the Grant No. USDA-NR1 2007-131G awarded by the USDA. The Government has certain rights in the invention.

FIELD OF INVENTION

The present invention relates to methods, reagents, apparatus, kits, and the like for detecting the fertility of a mammal by evaluating the binding ability of sperm. The present invention provides for an easy, practical, fast and reproducible test to determine whether sperm from an individual mammal, such as a boar, can both bind and undergo acrosomal exocytosis.

BACKGROUND

Selecting animals, such as boars, with high quality sperm is critical for livestock farming/industry. For example, pork is the most consumed meat in the world, over 100 million tons of pork meat is produced every year, and there are two billion living domestic pigs at any given time. The US and the EU constitute a third of the production, and almost all piglets born there are the result of artificial insemination (AI). AI has dramatically increased the genetic variability of these animals and enhanced the overall quality of the pork, especially the reduction of fat content that previously made it undesirable for many potential customers. It is critical that the boars, as well as other mammalian males, selected for breeding have high quality sperm, so that the success rate of fertilization is high and insemination results in frequent and healthy offspring.

Mammalian fertilization is initiated when sperm bind to the specialized extracellular matrix surrounding the egg, known as the zona pellucida (ZP). This binding triggers a signaling cascade that leads directly to acrosomal exocytosis (Yanagimachi, 1994). The induction of this reaction is indicated microscopically by the fusion of the plasma membrane with the outer membrane of the acrosome, a sperm organelle lying just beneath the plasma membrane. The fused membranes undergo vesiculation and fenestration, forming membrane blebs that slough off the sperm head, revealing the inner acrosomal membrane. Adhesion molecules on this membrane interact with the ZP, enabling the acrosome-reacted sperm to bind to and penetrate this matrix. The sperm enters the perivitelline space and fuses with the egg cell, thus completing the cellular binding events necessary for fertilization (Lopo et al., 1982; Yanagimachi, 1994).

Evidence that carbohydrate recognition plays a major role in mediating sperm-egg binding was initially obtained in several invertebrate marine species (Lopo et al., 1982; Mengerink and Vacquier, 2001; Monroy, 1965; Vacquier and Moy, 1977). Based on these findings, the natural assumption was that mammalian sperm-egg binding would also rely on lectin-like interactions. Defining the molecular basis underlying this binding event has been the subject of a major research effort ever since murine and porcine ZP (pZP) glycoproteins were initially isolated over three decades ago (Bleil and Wassarman, 1978; Dunbar et al., 1978). This interaction has also been investigated in the rat, hamster, and guinea pig (Tulsiani et al., 1997). Recently, the inventors' study also implicated the sialyl-Lewis$^x$ sequence expressed on the human ZP as a carbohydrate ligand that mediates human gamete binding (Pang et al., 2011).

Many studies indicate that a lectin-like egg binding protein (EBP) positioned on the mammalian sperm plasma membrane binds to glycans presented on the ZP during the initial stages of fertilization (Clark, 2010; Tulsiani et al., 1997). Evidence obtained in a somatic cell adhesion system also supports the presence of lectin-like EBPs on the surface of porcine and murine sperm (Clark, 2010; Sutton-Smith et al., 2007).

Classical lectins often display apparent $K_d$ values in the nM range for glycoconjugates bearing their multivalent ligands (Dam et al., 2009). The possibility was considered that lectin-like EBPs require the appropriate presentation of carbohydrate ligands to mediate sperm binding, but do not require the simultaneous recognition of the ZP protein backbone. The glycans associated with mouse, pig and human ZP glycoproteins have now been sequenced (Clark, 2010; Hedrick, 2008 Noguchi and Nakano, 1993; Pang et at, 2011). Glycomic analyses of many glycoproteins unrelated to reproductive function have also been performed since 1970 (North et al, 2009). However, a direct testing of sperm fertility based on binding activity and abilities to undergo acrosomal exocytosis has never been considered or successfully attempted.

Therefore, there is a need to provide new testing methods and apparatus for determining fertility of a mammal with specific tests focusing on sperm motility, morphology, binding ability to an egg and ability for undergoing acrosomal exocytosis.

SUMMARY OF THE INVENTION

The present invention provides a new apparatus/system, e.g., reagents and kits, for determining the fertility of mammalian sperm based on a specific sperm-binding test that mimics sperm binding to an egg and ability to undergo the acrosome reaction. Certain embodiments comprise surface-modified heads with a compound or conjugates containing a carbohydrate sequence, which is identical or in 85% homology with the terminal carbohydrate sequences that are associated with the mammalian zona-pellucida (ZP) glycoproteins, in a standard in vitro fertilization media. AFFI-GEL® (Bio-Rad, Hercules, Calif.) beads may be employed, and the compound or conjugates with the desired carbohydrate sequence can be immobilized on the beads at saturating density to facilitate rapid and accurate testing.

According to one embodiment of the invention, a mammalian sperm fertility test comprises a certain amount of AFFI-GEL® beads surface-modified with a compound or conjugates containing lacNAc (Galβ1-4GlcNAc sequence) in a standard in vitro fertilization media. Furthermore, the compound or conjugate is bovine thyroglobulin, porcine N-glycan, or porcine O-glycan. a mimic of bovine thyroglobulin, porcine N-glycan, or porcine O-glycan, or a combination thereof. In certain embodiments, the sperm is from a boar.

According to another embodiment of the invention, a bovine sperm fertility test comprises a certain amount of AFFI-GEL® beads surface-modified with a compound or conjugates containing terminal high mannose sequence ($Man_5GlcNAc_2$) in a standard in vitro fertilization media.

According to yet another embodiment of the invention, a human sperm fertility test comprises a certain amount of AFFI-GEL® beads surface-modified with a compound or conjugates containing sialyl-Lewis$^x$ sequence in a standard in vitro fertilization media.

The invention also provides testing methods for evaluating fertility of mammalian sperm based on a specific sperm-binding test mimicking the sperm's binding to an egg and subsequently undergoing the acrosome reaction. The inventive testing method comprises the step of 1) providing a certain amount of surface-modified beads with a compound conjugates containing a carbohydrate sequence, which is identical or in 85% homology with the terminal carbohydrate sequences that are associated with the mammalian ZP glycoproteins, in a standard in vitro fertilization media, and 2) adding the sperm into the fertilization media. To achieve a quantitative result, the inventive testing method may further comprise the step of removing the sperm unbounded to the bead, and counting the sperm bound to the bead.

Certain embodiments of the invention are drawn to a method of evaluating the ability of non-human mammalian sperm to bind to a mammalian egg. Such methods comprise combining a sample of non-human mammalian sperm, a media that is conducive to maintaining the physiological activity of the sperm, and at least one substrate that comprises on at least a portion of its surface a compound or conjugate. The compound or conjugate comprises a Galβ1-4GlcNAc terminal carbohydrate. The combination allows for at least a portion of the sample of non-human mammalian sperm to bind to the substrate. Binding of sperm to the substrate comprising the compound or conjugate is indicative of the binding of sperm to a mammalian egg. The combination formed may be incubated for a period of time, for example about 30 minutes, to allow for at least a portion of the sample of non-human mammalian sperm to bind to the substrate. Next, the sperm bound to the substrate is visualized or quantitated, thereby evaluating the ability of non-human mammalian sperm to bind to a mammalian egg. In certain embodiments, the method further comprises removing at least a portion of the unbound sperm before visualizing or quantitating the sperm bound to the substrate. This may be done to increase the sensitivity or accuracy of the visualization or quantitation. In certain embodiments, the substrate comprises a crosslinked agarose bead. In certain embodiments, the compound or conjugate is attached to the surface of a specimen slide, dish, or well of a microtiter plate and/or the compound or conjugate is fixed for use in flow cytometry. In certain embodiments, the mammalian sperm is equine or porcine. In certain embodiments, the mammalian sperm is from a cow, sheep, goat, dog, cat, rabbit, mouse, rat, hamster, or guinea pig. In certain embodiments, the compound or conjugate is bovine thyroglobulin, porcine N-glycan, or porcine O-glycan, a mimic of bovine thyroglobulin, porcine N-glycan, or porcine O-glycan, or a combination thereof.

In certain embodiments, the method of evaluating the ability of non-human mammalian sperm to bind to a mammalian egg comprises combining a sample of equine or porcine mammalian sperm, a media that is conducive to maintaining the physiological activity of the sperm, and at least one substrate that comprises on at least a portion of its surface a compound or conjugate, wherein the compound or conjugate is bovine thyroglobulin, porcine N-glycan, or porcine O-glycan, a mimic of bovine thyroglobulin, porcine N-glycan, or porcine O-glycan, or a combination thereof and the substrate comprises a crosslinked agarose bead. The combination to allows for at least a portion of the sample of mammalian sperm to bind to the substrate. The binding of sperm to the substrate comprising the compound or conjugate is indicative of the binding of sperm to a mammalian egg. The combination formed may be incubated for a period of time, for example about 30 minutes, to allow for at least a portion of the sample of non-human mammalian sperm to bind to the substrate. Next, the sperm bound to the substrate is visualized or quantitated, thereby evaluating the ability of non-human mammalian sperm to bind to a mammalian egg. In certain embodiments, the method further comprises removing at least a portion of the unbound sperm before visualizing or quantitating the sperm bound to the substrate. This may be done to increase the sensitivity or accuracy of the visualization or quantitation. In certain embodiments, the compound or conjugate is attached to the surface of the substrate in a saturating concentration. In certain embodiments, the compound or conjugate is bovine thyroglobulin of a mimic thereof and in certain embodiments, the mammalian sperm is porcine and the compound or conjugate is bovine thyroglobulin or a mimic thereof. In certain embodiments, the compound or conjugate is porcine N-glycan or a mimic thereof and in certain embodiments, the mammalian sperm is porcine and the compound or conjugate is porcine N-glycan or a mimic thereof. In certain embodiments, the compound or conjugate is porcine O-glycan or a mimic thereof and in certain embodiments, the mammalian sperm is porcine and the compound or conjugate is porcine O-glycan or a mimic thereof. In certain embodiments, the mammalian sperm is equine and the compound or conjugate is bovine thyroglobulin or a mimic thereof. In certain embodiments, the mammalian sperm is equine and the compound or conjugate is porcine N-glycan or a mimic thereof. In certain embodiments, the mammalian sperm is equine and the compound or conjugate is porcine O-glycan or a mimic thereof. In certain embodiments, the mammalian sperm is bovine and the compound or conjugate is bovine thyroglobulin or a mimic thereof. In certain embodiments, the mammalian sperm is bovine and the compound or conjugate is porcine N-glycan or a mimic thereof. In certain embodiments, the mammalian sperm is bovine and the compound or conjugate is porcine O-glycan or a mimic thereof. In certain embodiments, the mammalian sperm is murine and the compound or conjugate is bovine thyroglobulin or a mimic thereof. In certain embodiments, the mammalian sperm is murine and the compound or conjugate is porcine N-glycan or a mimic thereof. In certain embodiments, the mammalian sperm is murine and the compound or conjugate is porcine O-glycan or a mimic thereof. In certain embodiments, the mammalian sperm is from a rat, rabbit, sheep, goat, guinea pig. cat, dog, or hamster, and the compound or conjugate is bovine thyroglobulin or a mimic thereof. In certain embodiments, the mammalian sperm is from a rat, rabbit, sheep, goat, guinea pig, cat, dog, or hamster, and the compound or conjugate is porcine N-glycan or a mimic thereof. In certain embodiments, the mammalian sperm is from a rat, rabbit, sheep, goat, guinea pig, cat, dog, or hamster, and the compound or conjugate is porcine O-glycan or a mimic thereof.

Certain embodiments are drawn to reagents for determining the ability of non-human mammalian sperm to bind to a mammalian egg. Such reagents comprise a substrate that comprises on at least a portion of its surface a compound or conjugate, wherein the compound or conjugate comprises a Galβ1-4GlcNac terminal carbohydrate. In certain embodiments, the substrate comprises a crosslinked agarose bead. In certain embodiments, the compound or conjugate is attached to the surface of the substrate in a saturating concentration. In certain embodiments, the compound or conjugate is attached to the surface of a specimen slide, dish, or well of a microtiter plate and/or the compound or conjugate is fixed for use in flow cytometry. In certain embodiments, the compound or conjugate is bovine thyrogiobulin, porcine N-glycan, or porcine O-glycan, a mimic of bovine thyroglobulin, porcine N-glycan, or porcine O-glycan, or a combination thereof.

In certain embodiments of a reagent for determining the ability of non-human mammalian sperm to bind to a mammalian egg, the reagent comprises a substrate that comprises on at least a portion of its surface a compound or conjugate, wherein the compound or conjugate is bovine thyroglobulin, porcine N-glycan, or porcine O-glycan, a mimic of bovine thyrogiobulin, porcine N-glycan, or porcine O-glycan, or a combination thereof and wherein the substrate comprises a crosslinked agarose bead. In certain embodiments, the compound or conjugate is attached to the surface of the substrate in a saturating concentration. In certain embodiments, the compound or conjugate is attached to the surface of a specimen slide, dish, or well of a microtiter plate and/or the compound or conjugate is fixed for use in flow cytometry.

Certain embodiments of the invention provide for a kit for determining the ability of non-human mammalian sperm to bind to a mammalian egg. Such kits comprise a compound or conjugate, wherein the compound or conjugate comprises a Galβ1-4GlcNac terminal carbohydrate along with at least one other reagent selected from the group consisting of: (i) a substrate to which the compound or conjugate may be attached and (ii) at least one component of a media that is conducive to maintaining the physiological activity of sperm. In certain embodiments, the substrate comprises a crosslinked agarose bead. In certain embodiments, the compound or conjugate is bovine thyroglobulin, porcine N-glycan, or porcine O-glycan, a mimic of bovine thyroglobulin, porcine N-glycan, or porcine O-glycan, or a combination thereof.

In certain embodiments of a kit for determining the ability of non-human mammalian sperm to bind to a mammalian egg, the kit comprises a compound or conjugate, wherein the compound or conjugate is bovine thyroglobulin, porcine N-glycan, or porcine O-glycan, a mimic of bovine thyroglobulin, porcine N-glycan, or porcine O-glycan, or a combination thereof along with at least one other reagent selected from the group consisting of: (i) a substrate that comprises a crosslinked agarose bead to which the compound or conjugate may be attached and (ii) at least one component of a media that is conducive to maintaining the physiological activity of sperm.

BRIEF DESCRIPTION OF DRAWINGS

FIG. 1 illustrates carbohydrate sequences associated with the ZP for human.

DETAILED DESCRIPTION OF INVENTION

The invention provides a simple and sensitive apparatus/systems and methods for determining fertility in a mammalian male based on a specific sperm-binding test mimicking the sperm's binding to an egg and subsequently undergoing the acrosome reaction. The embodiments of the invention focus on sperm motility and morphology and enables a user to better predict the fertility of a specific male mammal and identify those with a high count of functional sperm.

Without being bound by theory, mammalian sperm-to-egg binding depends primarily on the recognition of a species-specific terminal carbohydrate sequence presented on glycans associated with zona-pellucida (ZP) glycoproteins. There are clear indications that sperm from diverse species express an egg binding protein (EBP) that has properties associated with classical lectins. Many lectins display dissociation constants ($K_d$) in the nM range for glycoconjugates bearing their multivalent ligands, indicating that a lectin-like EBP alone can mediate robust sperm binding. Thus, a glycoprotein that bears glycans that are similar to those expressed on a ZP matrix can mediate sperm binding, in the absence of a ZP protein backbone.

One aspect of the invention provides that the inventive apparatus/system for determining the fertility of sperm from a particular mammal comprises surface-modified beads with a compound or conjugates containing a carbohydrate sequence, which is identical or has 85% homology with the terminal carbohydrate sequences that are associated with the mammalian ZP glycoproteins, in a standard in vitro fertilization media. The AFFI-GEL® bead may be employed, and the compound or conjugates with the desired carbohydrate sequence is immobilized on the bead at saturating density to facilitate the speeding and accurate testing.

In certain embodiments, the apparatus/system is a reagent for determining the ability of mammalian sperm to bind to a mammalian egg. In certain embodiments, the mammalian sperm is from a non-human mammal. Illustrative, non-limiting examples of such include pigs (porcine), cows (bovine), horses (equine), sheep, goats, mice (murine), rats, rabbits, hamsters, and guinea pigs. The reagent comprises a substrate that comprises on at least a portion of its surface a compound or conjugate. In certain embodiments, the compound or conjugate is a glycoprotein. In certain embodiments, the substrate is one capable of binding to a glycoprotein, such as, but not limited to, one comprising a crosslinked agarose bead. AFFI-GEL® beads are an illustrative type of crosslinked agarose beads capable of binding to a glycoprotein. In certain embodiments, the compound or conjugate comprises a Galβ1-4GlcNac terminal carbohydrate. Non-limiting, illustrative examples of the compound or conjugate include bovine thyroglobulin, porcine N-glycan, porcine O-glycan, mimics of bovine thyroglobulin, porcine N-glycan, porcine O-glycan, or a combination thereof. In certain embodiments the compound or conjugate is attached to the surface of the substrate in a saturating concentration. Without being hound by theory, attaching the compound or conjugate to the surface of the substrate in a saturating concentration reduces or even eliminates the accessible region of the surface of the substrate such that only the compound or conjugate on the surface is accessible, thus mimicking the egg surface. Further, in order to increase for example ease, throughput, parallel processing, etc., the substrate may be attached to the surface of a specimen slide, dish, or well of a microtiter plate, or otherwise fixed for use in flow cytometry.

Certain embodiments of the invention are drawn to a new testing method for evaluating fertility of mammalian sperm based on a specific sperm-binding test mimicking the sperm's binding to an egg and subsequently undergoing the acrosome reaction. Such embodiments comprise the steps of 1) providing a certain amount of surface-modified beads with a compound or conjugate containing a carbohydrate sequence, which is identical or in 85% homology with the terminal carbohydrate sequences that are associated with the mammalian ZP glycoproteins, in a standard in vitro fertilization media, and 2) adding the sperm into the fertilization media. To achieve a quantitative result, the inventive testing method may further comprise the step of removing the sperm unbounded to the bead, and counting the number of sperm bound to the bead.

Certain embodiments are drawn to methods of evaluating the ability of mammalian sperm to bind to a mammalian egg. The mammal may be a non-human mammal such as, but not limited to pigs (porcine), cows (bovine), horses (equine), sheep, goats, mice (murine), rats, rabbits, hamsters, and guinea pigs. In certain embodiments, the non-human mammal is porcine or equine. In certain embodiments, the method comprises forming a combination that comprises: (i) a sample of mammalian sperm, (ii) a media that is conducive to maintaining the physiological activity of the sperm, and (iii) at least one substrate that comprises on at least a portion of its surface a compound or conjugate, wherein the compound or conjugate comprises a Galβ1-4GlcNAc terminal carbohydrate. One of ordinary skill in the art will recognize that "forming the combination" can be accomplished in a number of various manners such as by placing the components in contact with each other in a well, dish, on the surface of a specimen slide, or within an apparatus such as in which a media and sample is flowed over or otherwise contacted with the substrate. The combination is formed to allow for at least a portion of the sample of mammalian sperm to bind to the substrate. For example, certain embodiments of a method of the invention are drawn to passing a sample of sperm across a fixed substrate and capturing at least a portion of the sperm sample that binds to the substrate, wherein the portion of the sperm sample that does not bind the substrate is not captured. The media may be any that is conducive to maintaining the physiological activity of the sperm, such as in vitro fertilization media. After the sperm is allowed to bind to the substrate, the sperm bound to the substrate may be visualized or quantitated. Visualization and quantitation of the bound sperm may be enhanced by fixing and/or staining the bound sperm. In certain embodiments, cytochemical or immuno histochemical staining of the bound sperm may be used to enhance visualization and quantitation. Quantitation may be done by various methods, for example, by manual counting of sperm or by automated counting using imaging or flow cytometry methods. In certain embodiments, all of the substrate surface coated with the compound or conjugate may be examined. In certain embodiments, only a portion of the substrate surface may be examined to determine the amount of sperm bound to that portion. The value obtained may be used to determine another value, such as a number or approximate number of all of the sperm bound in the sample. The quantity of sperm bound to any amount of substrate may also be used to calculate, for example, the amount or approximate amount of sperm bound per area of substrate surface, or per concentration of substrate, or per density of compound or conjugate available for binding, etc. The quantity of sperm bound in one sample may also be compared to the quantity of sperm bound in one or more other samples, to determine a ratio. The quantity of sperm bound or the ratio of sperm bound may be useful in evaluating the ability of a sample of sperm to bind to the carbohydrate sequence which may be representative and/or predictive of its ability to bind to an egg. In certain embodiments, bound sperm may undergo acrosomal exocytosis, which can be detected by the binding of FITC-labeled peanut agglutinin (*Arachis hypogaea*) to the exposed inner acrosomal membranes and acrosomal shrouds. In certain embodiments, unbound sperm may be removed before visualizing or quantitation in order to improve the sensitivity of these steps. The substrate, compound or conjugate, etc, are as previously described herein. For example, in certain embodiments, the substrate comprises a crosslinked agarose bead. The compound or conjugate may be attached to the surface of the substrate in a saturating concentration. In certain embodiments, the compound or conjugate is a glycoprotein. For example, the compound or conjugate may be selected from the group consisting bovine thyroglobulin, porcine N-glycan, porcine O-glycan, or a combination thereof. In certain embodiments, the substrate may be attached to the surface of a specimen slide, dish, or well of a microtiter plate, or otherwise fixed for use in flow cytometry.

Certain embodiments of the invention are drawn to a kit for determining the ability of mammalian sperm to bind to a mammalian egg consistent with the methods described herein. In certain embodiments, the kit comprises a compound or conjugate, wherein the compound or conjugate comprises a Galβ1-4GlcNac terminal carbohydrate. The kit also comprises at least one other reagent selected from the group consisting of (i) a substrate to which the compound or conjugate may be attached and (ii) at least one component of a media that is conducive to maintaining the physiological activity of sperm. Such a kit could be provided with the compound or conjugate attached to the substrate or allow for the user to attach the compound or conjugate to the substrate prior to use Consistent with the aforedescribed embodiments of reagents and methods of the invention, the substrate may comprise a crosslinked agarose bead. The compound or conjugate may be selected from the group consisting bovine thyroglobulin, porcine N-glycan, porcine O-glycan, or a combination thereof.

The carbohydrate sequences associated with the ZP from human, mouse, bovine, porcine, and other mammals have now been rigorously defined by the inventors and other investigators (Clark, 2010; Hedrick, 2008; Pang et al., 2011). Thus, the aforesaid compounds or conjugates may be produced accordingly to contain the terminal carbohydrate sequence specific to each individual species, which in turn extends the inventive testing apparatus and method to many mammalian species, including but not limited to porcine, equine, and human.

FIG. 1 illustrates carbohydrate sequences associated with the ZP for human. As shown in FIG. 1, human ZP glycoproteins express a very high density of N-glycans bearing sialyl-Lewis$^x$ sequences.

The following disclosed examples are merely representative of the invention which may be embodied in various forms. Thus, specific structural, functional, and procedural details disclosed in the following examples are not to be interpreted as limiting:

EXAMPLES

Boar Sperm Fertility Test. The boar sperm fertility test comprises a certain amount of AFFI-GEL® beads surface-modified with a compound or conjugates containing Galβ1-4GlcNAc sequence (for example selected from bovine thyroglobulin, porcine N-glycan, porcine O-glycan, or mimics thereof) in a standard in vitro fertilization media. AFFI-GEL® beads can couple (attach) up to 35-40 mg of protein per packed ml of beads. In order to attach the beads at saturating conditions to produce a saturating concentration, one nil of packed beads is incubated with 2-3 ml of coupling buffer containing 100 mg of bovine thyroglobulin.

Bovine thyroglobulin (bTg) coated beads are preferred for the boar sperm testing apparatus. Perusal of the glycobiological literature indicated a potential overlap in glycosylation between bovine thyroglobulin (bTg) and porcine ZP (pZP). pZP glycoproteins express substantial amounts of sulfated and sialylated N- and O-glycans, based upon the results of many studies. Neutral tri- and tetraantennary N-glycans terminated with lacNAc (Galβ1-4GlcNAc) sequences have been implicated as the major ligands for boar sperm-ZP binding. Limited glycomic analyses have been performed on bTg, but nonetheless they indicated a potential overlap in glycosylation with pZP.

To further confirm this relationship, bTg has been subjected to glycomics and sulfoglycomics analysis by using modern mass spectrometric methods. Substantial structural overlaps in glycosylation between bTg and pZP glycoproteins have been confirmed.

During a particular boar sperm fertility test, tag was coupled at saturating concentrations to agarose beads by employing N-hydroxysuccinimide based reaction. Boar sperm were capacitated and incubated under standard pig IVF conditions before being incubated with bTg coated beads. Sperm bound rapidly and robustly to these beads, just as they did to in vitro matured porcine egg controls. After 30 minutes, the bound sperm underwent acrosomal exocytosis, which was detected by the binding of FITC-labeled peanut agglutinin (*Arachis hypogaea*) to the exposed inner acrosomal membranes and acrosomal shrouds. Bovine sperm did not bind to these beads under optimal conditions for fertilization, nor did they undergo acrosomal exocytosis.

These studies provide compelling evidence that immobilized bTg mediates boar sperm binding and the induction of acrosomal exocytosis. These results clearly implicate: 1) bTg glycans in these biological activities, 2) the ability of the beads modified with bTg glycans to mimic porcine eggs, and 3) the advantage of the test for assessing the fertility of boars, especially prior to artificial insemination and IVF cycles.

While the invention has been described in connection with specific embodiments thereof, it will be understood that the inventive device is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth.

REFERENCES

Bleil, J. D., and Wassarman, P. M. (1978). Identification and characterization of proteins of zona pellucida . . . 1 Cell Biol 79, A173.
Clark, G. F. (2010). The mammalian zona pellucida: a matrix that mediates both gamete binding and immune recognition? Syst Biol Reprod Med 56, 349-364.
Dam, T. K., Gerken, T. A., and Brewer, C. F. (2009). Thermodynamics of multivalent carbohydrate-lectin cross-linking interactions: importance of entropy in the bind and jump mechanism. Biochemistry 48, 3822-3827.
Dunbar, B. S., Wardrip, N. J., and Hedrick, J. L. (1978). Isolation and physicochemical properties of porcine zona pellucida. J Cell Biol 79, A163.
Hedrick, J. L. (2008). Anuran and pig egg zona pellucida glycoproteins in fertilization and early development. Int J Dev Biol 52, 683-701.
Lopo, A. C., Glabe, C. G., Lennarz, W. J., and Vacquier, V. D. (1982). Sperm-egg binding events during sea urchin fertilization. Ann N Y Acad Sci 383, 405-425.
Mengerink, K. J., and Vacquier, V. D. (2001). Glycobiology of sperm-egg interactions in deuterostomes. Glycobiology 11, 37R-43R.
Monroy, A. (1965). Chemistry and Physiology of Fertilization (New York: Holt, Rinehart and Winston).
Noguchi, S., and Nakano, M. (1993). Structural characterization of the N-linked carbohydrate chains from mouse zona pellucida glycoproteins ZP2 and ZP3. Biochim Biophys Acta 1158, 217-226.
North, S. J., Hitchen, P. G., Haslam, S. M., and Dell, A. (2009). Mass spectrometry in the analysis of N-linked and O-linked glycans. Curr Opin Struct Biol 19, 498-506.
Pang, P. C., Chiu, P. C., Lee, C. L., Chang, L. Y., Panico, M., Morris, H. R., Haslam, S. M., Khoo, K. H., Clark, G. F., Yeung, W. S., et al. (2011). Human sperm binding is mediated by the sialyl-Lewis(x) oligosaccharide on the zona pellucida. Science 333, 1761-1764.
Sutton-Smith, M., Wong, N. K., Khoo, K. H., Wu, S. W., Yu, S. Y., Patankar, M. S., Easton, R., Lattanzio, F. A., Morris, H. R., Dell, A., et al. (2007). Analysis of protein-linked glycosylation in a sperm-somatic cell adhesion system. Glycobiology 17, 553-567.
Tulsiani, D. R. P., Yoshida-Komiya, H., and Araki, Y. (1997). Mammalian fertilization: a carbohydrate mediated event. Biol Reprod 57, 487-494.
Vacquier, V. D., and Moy, G. W. (1977). Isolation of bindin: the protein responsible for adhesion of sperm to sca urchin eggs. Proc Natl Acad Sci U S A 74, 2456-2460.
Yanagimachi, R. (1994). Mammalian fertilization. In Physiology of reproduction, E. Knohil, and J. D. Neill, eds. (New York: Raven Press), pp. 189-317.

What claimed is:

1. A method of evaluating the ability of non-human mammalian sperm to bind to a mammalian egg, the method comprising:
   (a) combining a sample of non-human mammalian sperm, a media that is conducive to maintaining the physiological activity of the sperm, and at least one substrate that comprises bovine thyroglobulin on at least a portion of its surface, to allow for at least a portion of the sample of non-human mammalian sperm to bind to the substrate, wherein the binding of sperm to the substrate is indicative of the binding of sperm to a mammalian egg; and
   (b) visualizing or quantitating the sperm bound to the substrate, thereby evaluating the ability of non-human mammalian sperm to bind to a mammalian egg.

2. The method of claim 1 further comprising removing at least a portion of the unbound sperm before visualizing or quantitating the sperm bound to the substrate.

3. The method of claim 1 wherein the substrate comprises a crosslinked agarose bead.

4. The method of claim 1 wherein the compound or conjugate is attached to the surface of a specimen slide, dish, or well of a microtiter plate.

5. The method of claim 1 wherein the compound or conjugate is fixed for use in flow cytometry.

6. The method of claim 1, wherein the mammalian sperm is equine or porcine.

7. The method of claim 1, wherein the mammalian sperm is porcine.

\* \* \* \* \*